United States Patent
Gillies et al.

(12) 
(10) Patent No.: US 6,648,869 B1
(45) Date of Patent: *Nov. 18, 2003

(54) VERTICALLY PLEATED DIAPER LINER

(75) Inventors: Ian W. Gillies, Mesa, AZ (US); Daniel R. Schlinz, Greenville, WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 169 days.

(21) Appl. No.: 08/774,758

(22) Filed: Dec. 30, 1996

(51) Int. Cl.$^7$ .............................. A61F 13/15; A61F 13/20
(52) U.S. Cl. ........................ 604/385.28; 604/385.101; 604/385.19; 604/385.29
(58) Field of Search ............................ 604/385.1, 385.2, 604/386, 387, 393–396, 385.101, 385.24–385.3, 385.08, 385.16, 385.19, 385.22, 385.23

(56) References Cited

U.S. PATENT DOCUMENTS

| | | | |
|---|---|---|---|
| 1,676,144 A | | 7/1928 | Houseknecht |
| 3,322,122 A | | 5/1967 | Daniel |
| 3,371,668 A | | 3/1968 | Johnson |
| 3,776,233 A | | 12/1973 | Schaar |
| 3,860,003 A | * | 1/1975 | Buell .................. 604/385.2 |
| 3,943,930 A | | 3/1976 | Schaar |
| 3,951,150 A | | 4/1976 | Schaar |
| 3,978,861 A | | 9/1976 | Schaar |
| 3,984,272 A | | 10/1976 | Teed |
| 3,995,638 A | | 12/1976 | Schaar |
| 3,995,640 A | | 12/1976 | Schaar |
| 3,999,547 A | | 12/1976 | Hernandez |
| 3,999,548 A | | 12/1976 | Hernandez |
| 4,081,301 A | * | 3/1978 | Buell |
| 4,182,333 A | | 1/1980 | Schaar |
| 4,246,900 A | | 1/1981 | Schroder |
| 4,253,461 A | * | 3/1981 | Strickland et al. |

(List continued on next page.)

FOREIGN PATENT DOCUMENTS

| | | |
|---|---|---|
| DE | 44 22 956 | 1/1996 |
| EP | 0 311 333 A2 | 4/1989 |
| EP | 0 585 904 | 3/1994 |
| FR | 2 495 899 | 6/1982 |
| FR | 2 561 078 | 9/1985 |

(List continued on next page.)

OTHER PUBLICATIONS

Patent Abstracts of Japan, vol. 014, No. 403 (C–0753), Aug. 31, 1990 & JP 02 152450 A (Honshu Paper Co., Ltd.), Jun. 12, 1990, see abstract figure 5.

*Primary Examiner*—Karin Reichle
(74) *Attorney, Agent, or Firm*—Brinks Hofer Gilson & Lione; G. Peter Nichols (57) ABSTRACT

An absorbent article such as a diaper includes a backsheet layer, a substantially liquid-permeable liner layer, and an absorbent body located between the backsheet and the liner. The backsheet and liner layers generally define a front waistband section, a rear waistband section, and an intermediate section, with the intermediate section interconnecting the front and rear waistband sections. The liner includes a plurality of spaced apart longitudinal upstanding ridges located at least in the intermediate section to provide barriers to transverse migration of body exudates. The upstanding ridges are formed by providing a plurality of laterally spaced apart and alternating longitudinally adhered liner portions and unadhered liner portions. Elastic members are located subjacent the unadhered portions and include a front end, a rear end, and a central portion disposed between the front and rear ends.

16 Claims, 5 Drawing Sheets

U.S. PATENT DOCUMENTS

| | | | |
|---|---|---|---|
| 4,413,996 A | 11/1983 | Taylor | |
| 4,501,587 A | 2/1985 | Enloe | |
| 4,560,380 A | 12/1985 | Tharel | |
| 4,610,679 A | 9/1986 | Matsushita | |
| 4,610,682 A | 9/1986 | Kopp | |
| 4,623,342 A | 11/1986 | Ito et al. | |
| 4,662,877 A | 5/1987 | Williams | |
| 4,681,579 A | 7/1987 | Toussant et al. | |
| 4,731,065 A | 3/1988 | Yamada | |
| 4,731,070 A | 3/1988 | Koci | |
| 4,731,071 A | 3/1988 | Pigneul | |
| 4,738,677 A | 4/1988 | Foreman | |
| 4,753,645 A | 6/1988 | Johnson | |
| 4,775,375 A | 10/1988 | Aledo | |
| 4,778,459 A | 10/1988 | Fuisz | |
| 4,781,711 A | 11/1988 | Houghton et al. | |
| 4,781,713 A | 11/1988 | Welch et al. | |
| 4,787,896 A | 11/1988 | Houghton et al. | |
| 4,790,839 A | 12/1988 | Ahr | |
| 4,795,454 A | 1/1989 | Dragoo | |
| 4,808,177 A * | 2/1989 | DesMarais et al. | 604/385.2 |
| 4,816,025 A | 3/1989 | Foreman | |
| 4,822,435 A | 4/1989 | Igaue et al. | |
| 4,828,555 A | 5/1989 | Hermansson | |
| RE33,106 E | 11/1989 | Beckestrom | |
| 4,891,258 A * | 1/1990 | Fahrenkrug | 604/385.1 |
| 4,892,536 A | 1/1990 | DesMarais et al. | |
| 4,895,568 A | 1/1990 | Enloe | |
| 4,904,251 A | 2/1990 | Igaue et al. | |
| 4,935,021 A * | 6/1990 | Huffman et al. | 604/385.2 |
| 4,938,755 A | 7/1990 | Foreman | |
| 4,968,312 A | 11/1990 | Khan | |
| 4,988,344 A | 1/1991 | Reising et al. | |
| 4,988,345 A | 1/1991 | Reising | |
| 4,990,147 A | 2/1991 | Freeland | |
| 4,994,052 A | 2/1991 | Kimura | |
| 5,021,051 A | 6/1991 | Hiuke | |
| 5,037,415 A | 8/1991 | Leroy et al. | |
| 5,062,840 A | 11/1991 | Holt et al. | |
| 5,064,489 A | 11/1991 | Ujimoto et al. | |
| 5,114,420 A | 5/1992 | Igaue et al. | |
| 5,134,007 A | 7/1992 | Reising et al. | |
| 5,171,236 A | 12/1992 | Dreier et al. | |
| 5,176,672 A | 1/1993 | Bruemmer et al. | |
| 5,197,959 A * | 3/1993 | Buell | 604/385.1 |
| 5,207,662 A | 5/1993 | James | |
| 5,211,641 A | 5/1993 | Roos et al. | |
| 5,269,775 A | 12/1993 | Freeland et al. | |
| 5,292,316 A | 3/1994 | Suzuki | |
| 5,300,053 A | 4/1994 | Genaro | |
| 5,330,459 A | 7/1994 | Lavon et al. | |
| 5,334,177 A | 8/1994 | Cohen | |
| 5,342,343 A * | 8/1994 | Kitaoka et al. | 604/385.2 |
| 5,389,095 A * | 2/1995 | Suzuki et al. | 604/385.2 |
| 5,413,570 A | 5/1995 | Enloe | |
| 5,417,680 A | 5/1995 | Kimura et al. | |
| 5,451,219 A | 9/1995 | Suzuki et al. | |
| 5,451,442 A | 9/1995 | Pieniak et al. | |
| 5,458,591 A | 10/1995 | Roessler et al. | |
| 5,462,541 A | 10/1995 | Bruemmer et al. | |
| H1511 H | 12/1995 | Chappell et al. | |
| 5,476,457 A | 12/1995 | Roessler et al. | |
| 5,476,458 A | 12/1995 | Glaug et al. | |
| 5,507,895 A | 4/1996 | Suekane | |
| 5,527,300 A | 6/1996 | Sauer | |
| 5,527,303 A | 6/1996 | Milby, Jr. et al. | |
| H1630 H * | 1/1997 | Roe et al. | 604/385.2 |
| 5,593,400 A * | 1/1997 | O'Leary | 604/400 |
| 5,746,732 A * | 5/1998 | Olsson et al. | 604/385.2 |
| 5,797,895 A * | 8/1998 | Widlund et al. | 604/385.24 |
| 5,876,390 A * | 3/1999 | Hall et al. | 604/385.2 |
| 5,891,124 A * | 4/1999 | Nomura et al. | |
| 6,436,081 B1 * | 8/2002 | Wada et al. | 604/385.01 |
| 2001/0021836 A1 * | 9/2001 | Kashiwagi | |
| 2002/0151861 A1 * | 10/2002 | Klemp et al. | 604/385.19 |

FOREIGN PATENT DOCUMENTS

| | | | |
|---|---|---|---|
| FR | 2 573 629 | | 5/1986 |
| GB | 2 242 610 A | | 9/1991 |
| GB | 2 263 622 A | | 4/1993 |
| JP | 3-188851 | * | 8/1991 |
| WO | 9302647 | * | 2/1993 ............ 604/385.2 |
| WO | WO 96/00545 | | 1/1996 |
| WO | WO 97/07764 | | 3/1997 |

* cited by examiner

VERTICALLY PLEATED DIAPER LINER

FIELD OF THE INVENTION

The present invention relates to absorbent articles such as disposable diapers, and more particularly to absorbent articles that have a longitudinally pleated liner to provide improved containment.

BACKGROUND OF THE INVENTION

The major function of absorbent articles, such as disposable diapers and adult incontinent briefs, is to absorb and contain body exudates. Such articles are intended to prevent body exudates from soiling, wetting, or otherwise contaminating clothing or other articles, such as bedding, that come in contact with the wearer. The most common mode of failure for such products occurs when body exudates leak out of the gaps between the absorbent article and the wearer's leg or waist to adjacent clothing because they are not immediately absorbed within the article. This is most evident with loose fecal material which is not easily absorbed by the absorbent article and tends to ride on the top surface of the absorbent article. Several solutions to this problem have been proposed.

For example, U.S. Statutory Inv. Reg. No. H1511 describes a flow regulator for an absorbent article that is positioned between the topsheet and the absorbent structure. The flow regulator is described as enhancing movement of fluid in the longitudinal direction while controlling movement of fluid in the transverse and z directions.

U.S. Pat. No. 4,808,177 describes a disposable diaper that has elastically contractible leg cuffs and a pair of floating inner cuffs that are positioned inboard of the leg cuffs to provided containment characteristics. The floating inner cuffs include a cuff layer, a base layer underlaying the cuff layer, a first seam that affixes a portion of the cuff layer to the base layer, a central seam that affixes another portion of the cuff layer to the base layer, an unadhered stand-up portion of the cuff layer between the first seam and the central seam, and a central elastic member subjacent the unadhered stand-up portion that has a pair of affixed portions and an unaffixed portion between the pair of affixed portions. A particular disadvantage to this proposed solution is that the diaper does not lay flat and therefore presents a packaging obstacle.

U.S. Pat. No. 4,892,536 describes a disposable diaper that has elastic strands disposed longitudinally nonadjacent a passageway on the liner so that the fit of the diaper is improved. The passageway permits communication of solid waste through the liner.

U.S. Pat. No. 4,895,568 describes an absorbent article with a resilient barrier member located in the intermediate section of the article. The barrier member includes transversely distributed elastic members that are connected to the liner layer to gather the liner and form ruffled panel regions, which define a plurality of transverse folds to inhibit longitudinal movement of body exudate between the front and the rear waistbands. The elastic members have an active longitudinal extent of not more than about 50 percent of the total length of the article. The barrier member does not inhibit lateral movement of body exudate.

U.S. Pat. No. 5,037,415 describes a diaper that has two longitudinal strips extending in the stretched state over the entire length of the diaper along the opposite longitudinal edges of the pad and disposed between the backsheet and the liner. Elastic elements are attached along the longitudinal length of the strips to define leg cuffs.

U.S. Pat. No. 5,451,219 describes a stretchable diaper that includes a liquid impermeable elastic sheet having a non-woven fabric secured to the elastic sheet in a continuous manner in one direction and intermittently in a second direction transverse to the first direction so that a plurality of parallel channels extend in the first direction. Absorbent material may be disposed in the channels.

PCT Application No. WO 96/00545 describes a sanitary napkin having an absorbent body and a liquid permeable layer that is provided with longitudinal folds that are formed by using a folding device. The folds have foot areas that are attached to the absorbent body or to a support layer that lies between the absorbent body and the liquid permeable layer.

While the above designs are for the most part acceptable, there still remains a need for a disposable diaper having improved containment.

SUMMARY OF THE INVENTION

In accordance with the present invention, a disposable absorbent article such as a diaper is provided. While the present invention will be particularly described in the form of a diaper, one of skill in the art will appreciate that it may be advantageously used with incontinent briefs, diaper holders, training pants, and the like. Generally, the absorbent article comprises a liquid impervious backsheet layer, a substantially liquid-permeable liner layer, and an absorbent structure disposed between the backsheet and liner layers. The backsheet and liner layers generally define a front waistband section, a rear waistband section and an intermediate or crotch region interconnecting the front and rear waistband sections with the intermediate or crotch region being disposed between a pair of leg openings, which may be elasticized.

Portions of the liner layer are adhered to the absorbent structure in a spaced apart longitudinal fashion to define a plurality of laterally alternating adhered liner portions and unadhered liner portions. The adhered liner portions may be intermittently or continuously adhered to the absorbent structure along at least a portion of their longitudinal length. In any event, throughout the following description and claims, except where expressly stated, the term adhered portion refers to that portion of the liner that is adhered to the absorbent structure either intermittently or continuously along at least a portion of its longitudinal length. The liner may also be directly or indirectly adhered to the absorbent structure.

At least one longitudinally extending elastic member is associated with and located subjacent at least some of the unadhered portions of the liner layer to create stand-up ridges. Preferably, at least one elastic member is associated with each unadhered portion of the liner layer. Thus, a plurality of longitudinal ridges are provided transversely across the intermediate or crotch region of the diaper. In one embodiment, the height of each ridge is substantially the same. In another embodiment, the height of each ridge may differ to create a ridge across the lateral dimension of the absorbent structure.

In a preferred embodiment, each elastic member has a front end, a rear end, and a central portion interconnecting the front and rear ends. The front and rear ends are in a relaxed state (i.e., they are not in an elastically contractible condition) while the central portion is in an elastically contractible condition. Preferably, the central portion includes a first end and a second end, with each of the first and second ends adhered to the liner to define a region of the elastic member between the first end and the front end and between the second end and the rear end that is in a relaxed state. More preferably, the central portion between the first and second end is intermittently adhered to the liner to operably gather the liner and form a ruffled ridge.

The present invention, therefore, advantageously provides a plurality of longitudinal ridges, the peaks of which will closely fit to the surface of the wearer's skin and will aid in reducing skin contamination by separating the skin from the absorbent pad. The troughs (or valleys) created by the upstanding ridges define lengthwise pockets to contain fecal matter and other body exudates and to create barriers that may reduce lateral movement of fecal matter toward the legs, Which should reduce leakage in the leg area. The ridges may also conceal fecal matter when the diaper is removed. Because the front and rear ends of the elastic members are in a relaxed state, the diaper is able to lie flat and will not curl so that is easier to put the diaper on the wearer.

In one embodiment of the present invention there is provided a disposable absorbent article with a front waistband and a back waistband being spaced from each other prior to installing the article on a wearer and a crotch portion disposed in a longitudinal direction between the front waistband and the back waistband and disposed in a lateral direction between a pair of leg openings. The article includes a liquid impervious backsheet; a liquid pervious bodyside liner having a body facing surface and a garment facing surface, wherein the garment facing surface has a plurality of spaced apart longitudinally extending adhered portions located in the crotch portion of the article to define a plurality of laterally alternating adhered and unadhered portions in the crotch portion of the article; an absorbent structure disposed between the liner and the backsheet; and, at least three elastic members disposed between the liner and the absorbent structure and comprising a front end, a rear end and a central portion disposed between the front and rear ends with the central portion being in an elastically contractible condition, each of the elastic members associated with and positioned subjacent an unadhered liner portion wherein each of the elastic members causes the respective associated superjacent unadhered liner portion to be spaced away from the absorbent structure forming at least three ridges.

BRIEF DESCRIPTION OF THE DRAWINGS

The invention will be more fully understood and further advantages will become apparent when reference is made to the following detailed description and accompanying drawings in which.

DETAILED DESCRIPTION OF THE INVENTION

The following detailed description is made in the context of an absorbent article comprising a disposable diaper. It is readily apparent, however, that the present invention can be used with other disposable articles, such as feminine care garments, incontinence garments, training pants and the like.

Figure 1:
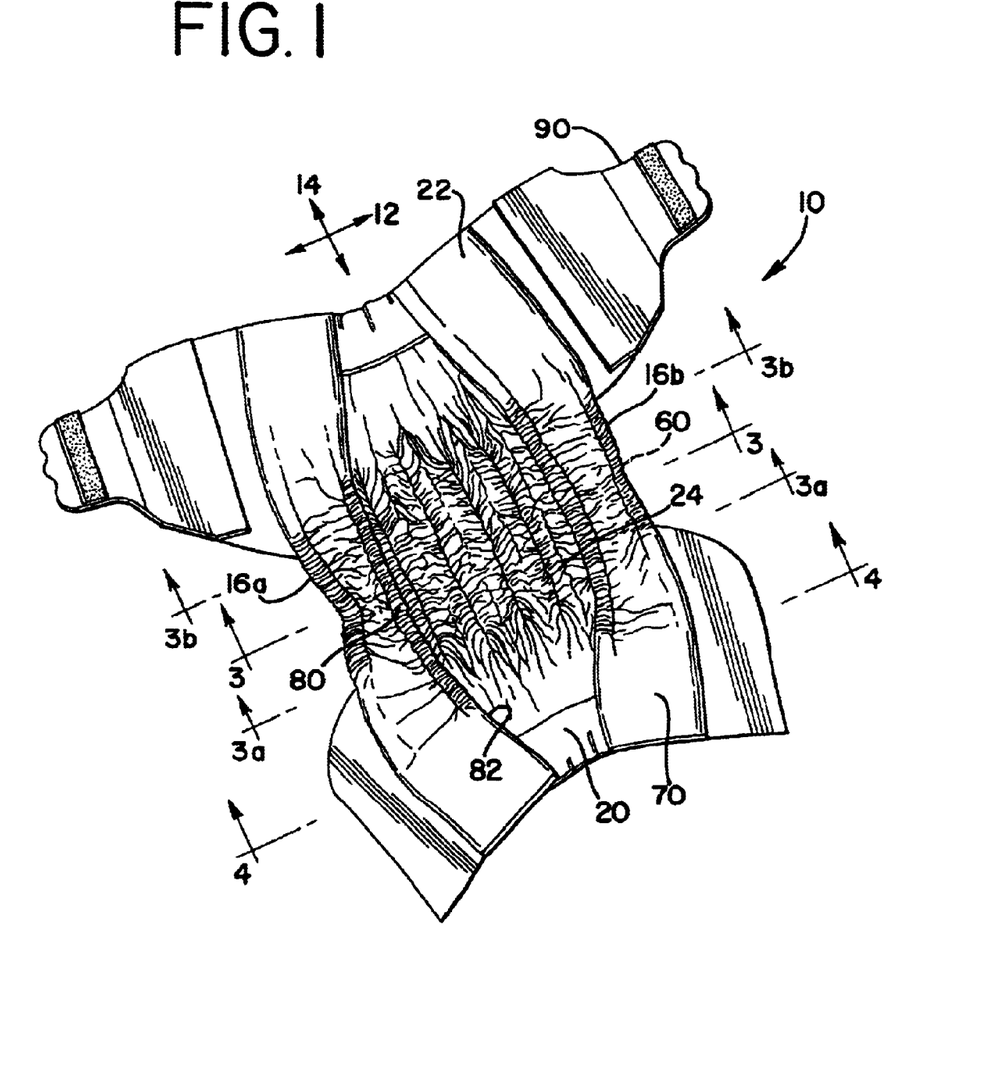
FIG. 1 is a top perspective view of a disposable diaper embodiment of the present invention, with the surface of the diaper that contacts the wearer facing the viewer.
Figure 2:
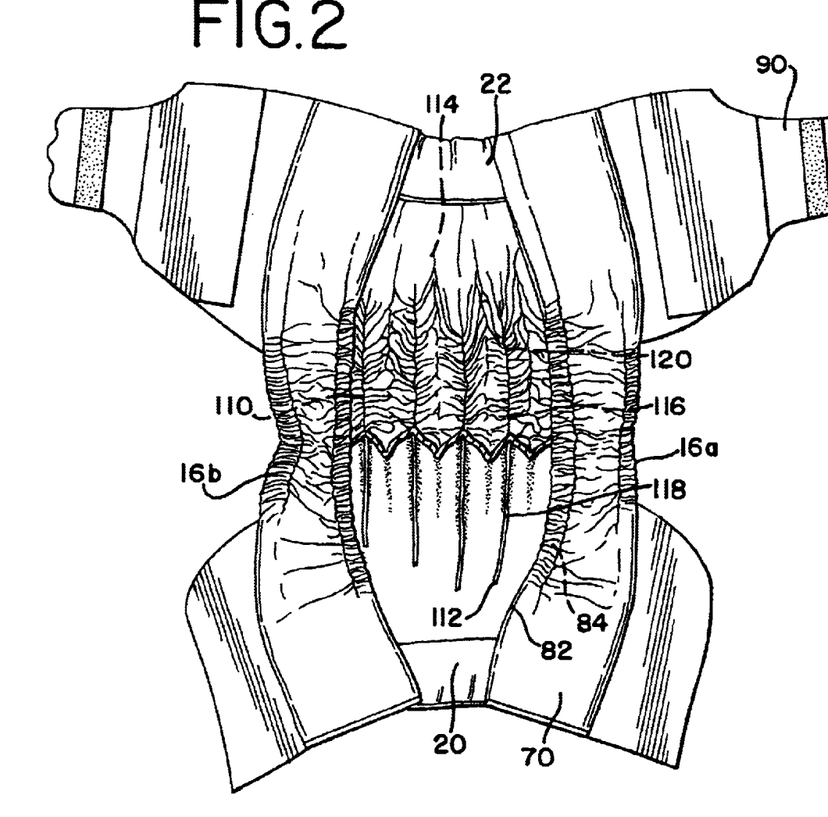
FIG. 2 is a top perspective of the diaper of FIG. 1 with a portion cut-away to reveal underlying structure.

With reference to FIGS. 1 and 2, an absorbent article, such as diaper 10 is shown with the surface of the diaper that contacts the wearer facing the viewer. The diaper 10 has a cross-wise, lateral dimension 12 and a length-wise, longitudinal dimension 14. The diaper 10 has laterally opposed side margins 16a, 16b, a front waistband 20, a back waistband 22, and an intermediate portion or crotch region 24 that interconnects the front and back waistband. The waistbands 20, 22 are arranged to encircle the front and back portions of the wearer's waist, and the intermediate portion is intended for placement between the wearer's legs.

The diaper comprises a substantially liquid-permeable liner 30, a substantially liquid impervious backsheet layer 40, and an absorbent structure 50 sandwiched between the liner and backsheet layers. The liner and backsheet may be generally coextensive, and may have a length and width dimension that are generally larger than the corresponding dimensions of the absorbent structure.

Leg elastic may be provided in the region of the side margins to provide elasticized, gathered leg openings. Containment flaps associated with the leg elastic may also be provided. Waist elastic may be provided in the region of the front and back waistbands. The liner, backsheet, absorbent structure, elastic members, and containment flaps may be assembled in a variety of well-known diaper configurations.

The liner presents a body-facing surface 32 which is compliant, soft-feeling, and non-irritating to the wearer's skin. Preferably, the liner is sufficiently porous to be liquid permeable, permitting liquid to penetrate through its thickness. A suitable liner may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The liner is typically used to help isolate the wearer's skin from liquids held in the absorbent structure. Various woven and nonwoven fabrics can be used for the liner. For example, the liner may be composed of a meltblown or spunbonded web of polyolefin fibers. The liner may also be a bonded-carded-web composed of natural and/or synthetic fibers. The liner fabrics may also be composed of a substantially hydrophobic and substantially nonwettable material, and the hydrophobic material may optionally be treated with a surfactant or otherwise processed to impart a desired level of wettability and hydrophilicity.

Figure 3:
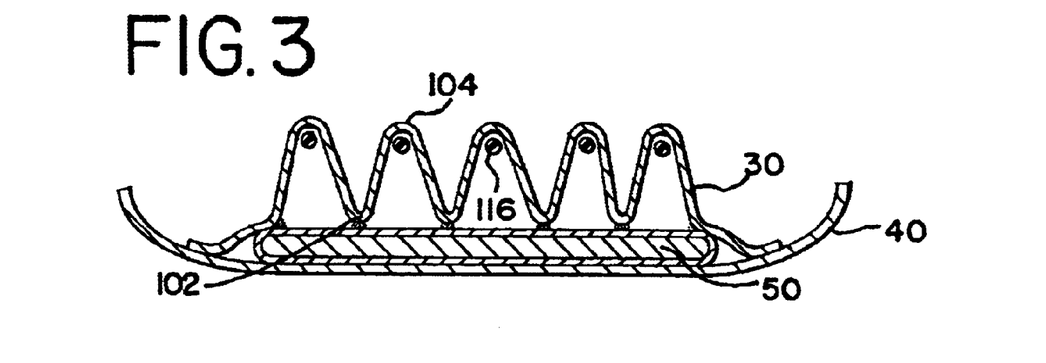
FIG. 3 is a fragmentary sectional view taken along line 3—3 of FIG. 1 with the carrier sheets and other structure not shown to more clearly illustrate the invention.
Figure 3A:
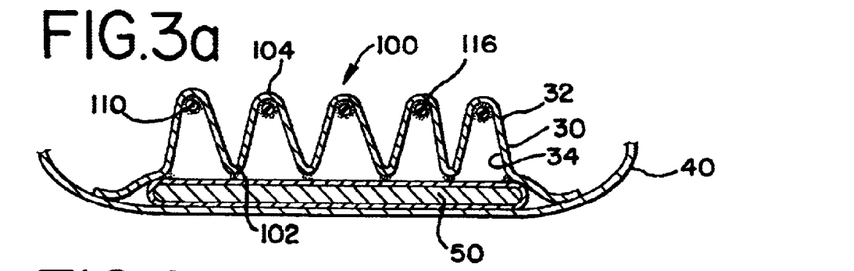
FIG. 3a is a fragmentary sectional view taken along line 3a—3a of FIG. 1, with the carrier sheets and other structure not shown to move clearly illustrate the invention.
Figure 3B:
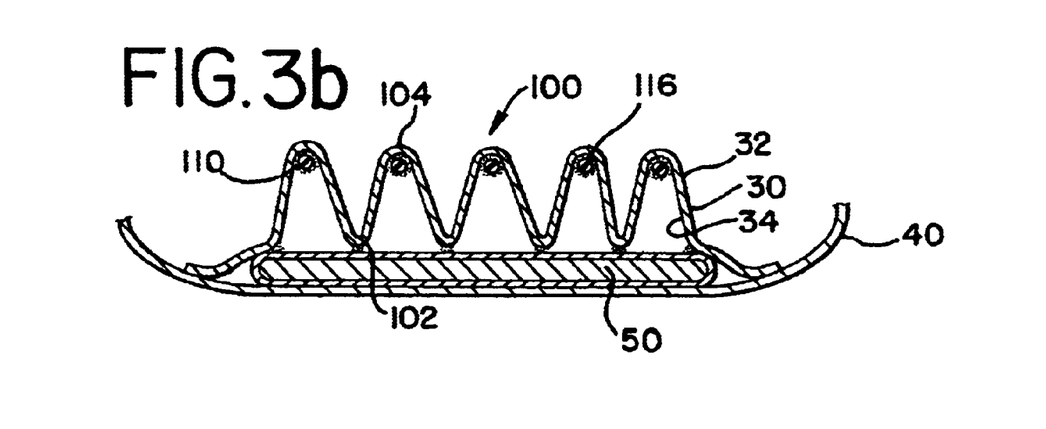
FIG. 3b is a fragmentary sectional view taken along line 3b—3b of FIG. 1, with the carrier sheets and other structure not shown to more clearly illustrate the invention.
Figure 4:
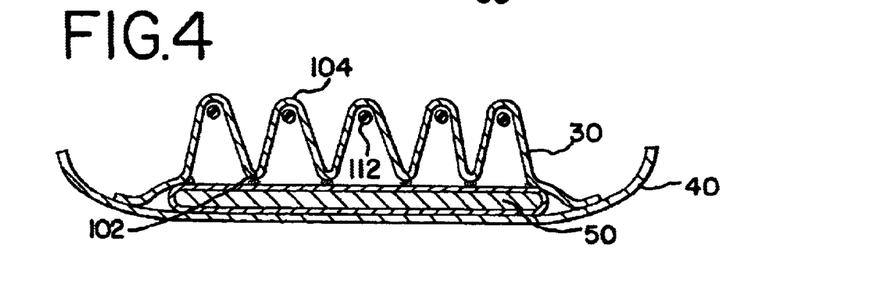
FIG. 4 is a fragmentary sectional view taken along section line 4—4 of FIG. 1 with the carrier sheets and other structure not shown to more clearly illustrate the invention.

An absorbent body, such as absorbent structure 50, is positioned between the liner 30 and the backsheet, as best seen in FIGS. 3 and 4. Alternatively, an intermediate structure 51 may be placed between the absorbent structure and the liner. The absorbent body has a construction which is generally compressible, conformable, non-irritating to the wearer's skin, and capable of absorbing and retaining liquid body exudates. It should be understood that, for the purposes of this invention, the absorbent structure may comprise a single, integral piece of material, or alternatively, may comprise a plurality of individual separate pieces of material which are operably assembled together. Where the absorbent structure comprises a single, substantially integral piece of material, the material could include the desired structural features formed into selected spatial regions thereof. Where the absorbent structure comprises multiple pieces, the pieces may be configured as discrete layers or as other nonlayered shapes and configurations. Furthermore, the individual pieces may be coextensive or non-coextensive, depending upon the requirements of the product. It is preferred, however, that each of the individual pieces be arranged in an operable, intimate contact along at least a portion of its boundary with at least one other adjacent piece of the absorbent structure. Preferably, each piece is connected to an adjacent portion of the absorbent structure by a suitable bonding and/or fiber entanglement mechanism, such as ultrasonic or adhesive bonding, or mechanical or hydraulic needling.

The absorbent structure may be manufactured in a wide variety of sizes and shapes (for example, rectangular, trapezoidal, T-shape, I-shape, hourglass shape, etc.) and from a wide variety of materials. The size and the absorbent capacity of absorbent structure should be compatible with the size of the intended wearer and the liquid loading imparted by the intended use of the absorbent article. Absorbent article structures suitable for use with the present invention are described in U.S. Pat. No. 5,192,606, the entire disclosure of which is hereby incorporated by reference in a manner that is consistent (not in contradiction) herewith.

Various types of wettable, hydrophilic fibrous material can be used to form the component parts of the absorbent structure. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made form inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

The entire absorbent structure can be overwrapped in a hydrophilic high wet-strength envelope web, such as a high, wet-strength tissue or a synthetic fibrous web. Such overwrapping web can also increase the in-use integrity of the absorbent structure. The web can be suitably bonded, such as with adhesive, to the absorbent structure and to other components of the product construction.

The backsheet 40 may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. The backsheet can help prevent the exudates contained in the absorbent structure from wetting articles such as bedsheets and overgarments which contact the diaper.

The backsheet may optionally be composed of a microporous, "breathable" material which permits vapors to escape from the absorbent structure while still preventing liquid exudates from passing through the backsheet. For example, the breathable backsheet may be composed of a microporous polymer film a nonwoven fabric which has been coated or otherwise treated to impart a desired level of liquid impermeability.

The size of the backsheet is typically determined by the size of the absorbent structure and the exact diaper design selected. The backsheet may have a generally T-shape, a generally I-shape or a modified hourglass shape, and may extend beyond the terminal edges of the absorbent structure by a selected distance.

The liner and backsheet are connected or otherwise associated together in an operable manner. As used herein, the term "associated" encompasses configurations in which the liner is directly joined to the backsheet by affixing the liner directly to the backsheet and configurations wherein the liner is joined to the backsheet by affixing the liner to intermediate members which in turn are affixed to the backsheet. The liner and backsheet can be affixed directly to each other in the diaper periphery by attachment means (not shown) such as an adhesive, sonic bonds, thermal bonds or any other attachment means known in the art. For example, a uniform continuous layer of adhesive, a patterned layer of adhesive, a sprayed pattern of adhesive or an array of separate lines, swirls or spots of construction adhesive may be used to affix the liner to the backsheet.

It should be readily appreciated that the above-described attachment means may also be employed to interconnect and assemble together the various other component parts of the article described herein.

As shown in FIGS. 3 and 4, the liner is disposed and secured in facing relation with the backsheet. The marginal side regions of the liner are operably connected to corresponding marginal side regions of the backsheet. Each of the attached marginal side regions of the liner and backsheet is located laterally outboard of the associated side edge region of the absorbent structure.

Leg elastic members 60 may be disposed along each of the longitudinal side edges. The leg elastic members can be connected to either or both of the liner and backsheet layers to provide elasticized side margins of the diaper article, and can be arranged to draw and hold the diaper against the legs of the wearer. Waist elastic members may also be disposed adjacent either or both of the end edges of the diaper to provide elasticized waistbands.

Preferably, the leg elastic members and the waist elastic members are secured to the diaper in an elastically contractible condition so that in a normal, under strain configuration, the elastic members effectively contract against the diaper. For example, the elastic members may be stretched and secured while the diaper is in an uncontracted condition. Alternatively, the diaper may be contracted, for example, by pleating, and the elastic members secured and connected to the diaper while the elastic members are in their unrelaxed or unstretched condition. Still other means, such as heat-shrink elastic material, may be used to gather and shrink the garment.

The leg elastic members may extend essentially along the complete length of crotch region 24 of the diaper. Alternatively, the leg elastic members may extend the entire length of the diaper or any other length suitable providing the arrangement of elastically contractible lines desired for the particular diaper design.

The leg and waist elastic members may have any of a multitude of configurations. For example, the width of the individual elastic members may be varied. The elastic members may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to the diaper with sprayed or swirled patterns of hot melt or other type of adhesive.

As shown in FIG. 1, the leg elastic member may comprise a carrier sheet 70 to which are attached a grouped set of elastics composed of a plurality of individual elastic strands. The elastic strands may intersect or be interconnected, or be entirely separated from one another. The shown carrier sheet may, for example, comprise a 0.002 cm thick film of unembossed polypropylene material. The shown elastic strands can, for example, be composed of LYCRA elastomer available from DuPont. Each elastic strand is typically within the range of about 620–1050 decitex (dtx). In addition, the leg elastic member may be generally straight or optionally curved.

As noted above, the diaper can include an elasticized containment flap 80 associated with the leg elastic member. For example, as shown in FIG. 1, the flap is provided as part of the carrier sheet 70. A movable edge region 82 of each containment flap includes a flap elastic member comprising one or more individual strands of elastomeric material. For example, a plurality of elastic strands may be configured in a spatially separated, generally parallel arrangement, and a suitable elastic strand can, for example, be composed of a LYCRA elastomer. The flap elastic member 84 is preferably connected to the movable edge of the containment flap in an elastically contractible condition such that the contraction of the elastic components thereof gathers and shortens the edge of the containment flap. As a result, the movable edge of each containment flap tends to position itself in a spaced relation away from the bodyside surfaces of the liner toward a generally upright and approximately perpendicular configuration, especially in the crotch section of the diaper. In the shown embodiment, for example, the moveable edge of the containment flap is connected to the flap elastic by partially doubling the flap material back upon itself by a limited amount which is sufficient to enclose the flap elastic.

The containment flaps may be constructed of a fibrous material which is similar to the material comprising the liner. Other conventional materials, such as polymer films, may also be employed. In other aspects of the invention, the containment flaps are constructed of a material which is permeable to gas, such as ambient air. Alternative configurations of the invention can include containment flaps that are constructed of a material which is resistant to a passage of aqueous liquid, such as urine, therethrough. For example, the containment flap may be constructed of a spunbond-meltblown-spunbond (SMS) laminate material.

Fastening means, such as tape tab fasteners 90 are typically applied to the back waistband region 22 of the diaper to provide a mechanism for holding the diaper on the wearer. Tape tab fasteners can be any of those well known in the art, and are typically applied to the corners of the diaper. For example, adhesive fasteners, mechanical fasteners, hook-and-loop fasteners, snaps, pins or buckles, may be used alone, or in combination. In the shown configuration, the fastener is the male or hook portion of hook-and-loop fastener that is constructed to releasably adhere to a landing zone patch (not shown) attached to the front waistband section of the diaper to provide a refastenable adhesive fastening system. In the shown configuration, therefore, the landing zone patch would include the female or loop portion of a hook-and-loop fastener.

In accordance with the principles of the present invention, a plurality of laterally spaced apart upstanding ridges 100 are provided in the liner at least in the intermediate region. Preferably, the ridges are aligned substantially parallel to the longitudinal axis 14. The ridges may be provided across the entire or a portion of the lateral dimension of the diaper. Preferably, the ridges are provided across substantially the entire lateral dimension of the absorbent structure. As stated above, the ridges are substantially longitudinally aligned and may extend the entire or a portion of the longitudinal dimension of the diaper.

Figure 8:
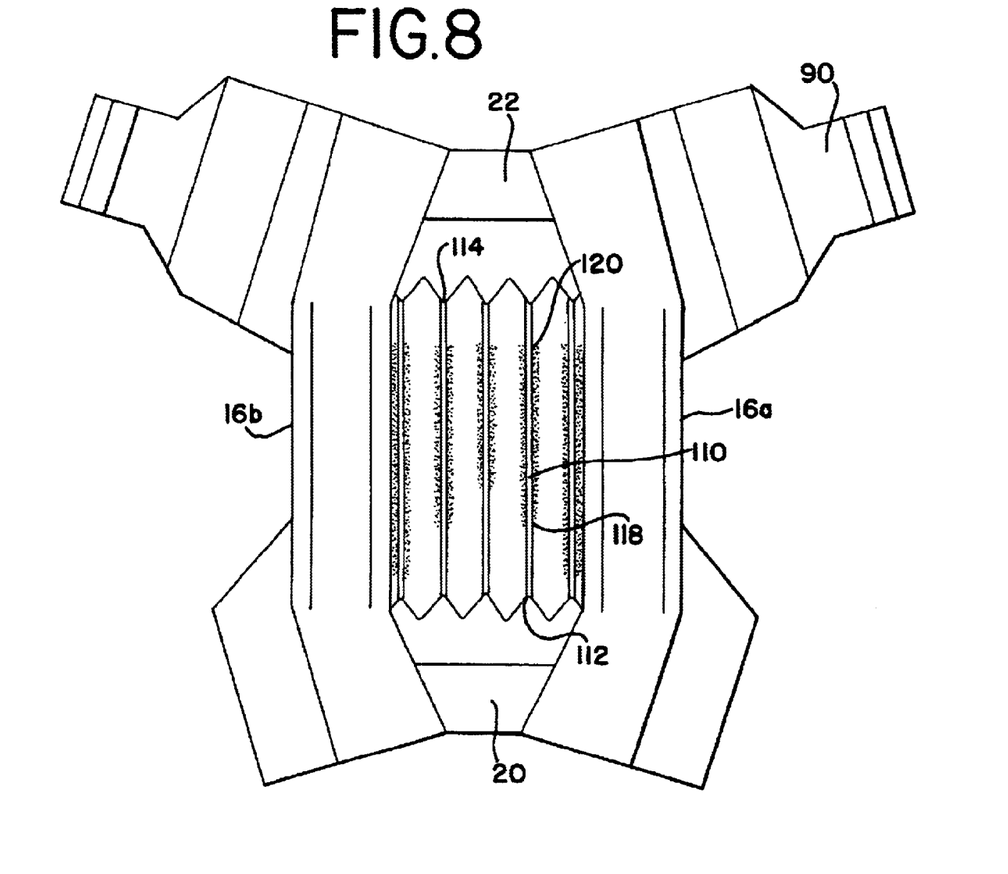
FIG. 8 is a is a top plan view of another embodiment of a disposable diaper of the present invention with a portion cut-away to reveal underlying structure. In this embodiment, the longitudinal length of the central portion of the elastic members differs. In particular, the central portion of the elastic member in the center has a longitudinally shorter length than the elastic members adjacent the side margins.

Also, each ridge may extend longitudinally an equal or different distance from the other ridges. For example, as shown in FIGS. 1 and 2, the central portion of each elastic member and, thus the upstanding ridge it forms, extends substantially the same longitudinal length at the front and rear of the diaper. In contrast, in FIG. 8, the central portion of each elastic member and, thus the upstanding ridge it forms, does not extend an equal length. Instead, in the middle of the diaper the central portion of the elastic member has a longitudinal length that is less than the longitudinal length of the central portion of the elastic member adjacent the side margins. In particular, in the embodiment shown, the rear end 120 of the central portion of each elastic member terminates at substantially the same region. However, the front end 118 of the central portion of each elastic member terminates at a different point.

Figure 6:
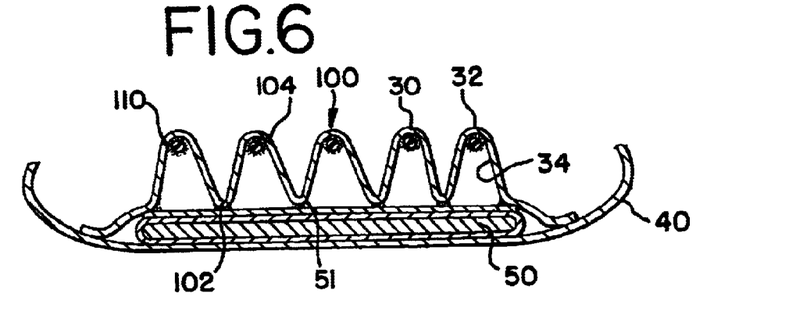
FIG. 6 is a fragmentary sectional view of another embodiment of a disposable diaper of the present invention taken along the crotch or intermediate portion of the diaper and with the carrier sheets and other structure not shown to more clearly illustrate the invention. In this embodiment the liner is indirectly adhered to the absorbent structure through an intermediate structure such as a nonwoven web.

The ridges are formed in the following manner. Portions of the liner layer, particularly the garment-facing surface 34, are adhered either directly or indirectly to the absorbent structure by any well-known method. In one embodiment, as best seen in FIGS. 3 and 4, spaced apart portions of the garment facing surface are adhered to the absorbent structure to define a plurality of laterally alternating adhered liner portions 102 and unadhered liner portions 104. The adhered liner portions may be adhered to the absorbent structure over the entire or a portion of the longitudinal length of the absorbent structure. In addition, the adhered portion may be continuously or intermittently adhered to the absorbent structure. Alternatively, the adhered portion may be indirectly adhered to the absorbent structure through an intermediate structure 51, such as a nonwoven web, as best seen in FIG. 6.

Figure 7:
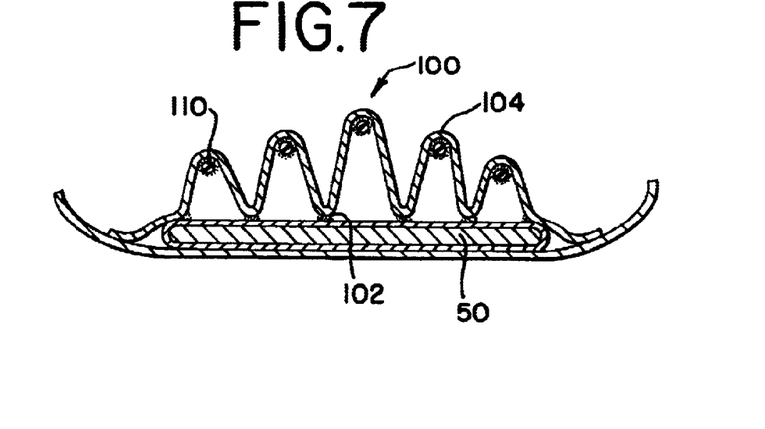
FIG. 7 is a partial fragmentary sectional view of another embodiment of a disposable diaper of the present invention taken along the crotch or intermediate portion of the diaper and with the carrier sheets and other structure not shown to more clearly illustrate the invention. In this embodiment, the height of each ridge differs and therefore creates a profile across the lateral dimension.

At least one elastic member 110 is associated with and located subjacent at least some of the unadhered portions of the liner to create an upstanding ridge. Preferably, at least one elastic member is associated with and located subadjacent each unadhered portion of the liner. Because the liner has alternating adhered and unadhered portions, the elastic members will define a plurality of spaced apart ridges across the lateral dimension of the absorbent structure. As shown in FIGS. 3, 4, and 6, the height of each ridge is substantially the same across the lateral dimension of the diaper. Alternatively, as shown in FIG. 7, the height of each ridge may differ to create a ridge profile across the lateral dimension of the diaper. In the particular embodiment shown in FIG. 7, the height of the ridge in the center of the diaper is greater than the height of each successive ridge to define an inverted "V" profile.

Each elastic member has a front end 112, a rear end 114, and a central portion 116 interconnecting the front and rear ends. The front and rear ends are in a relaxed state (i.e., they are not in an elastically contractible condition) while the central portion is in elastically contractible condition. Thus, when the diaper is stretched and put onto the wearer, the central portion of the elastic member causes the unadhered portion of the liner to stand up thereby creating a ridge and separating the wearer's body from the absorbent structure. Yet, because the front and rear ends of the elastic member are in a relaxed state the ends of the diaper will lie substantially flat when the diaper is removed from the packaging prior to installing on the wearer.

Preferably, the central portion includes a first end 118 and a second end 120 with each end attached to the garment facing surface of the liner to define a region of the elastic member between the first end and the front end and between the second end and the rear end that is in a relaxed state and another region between the first and the second end that is in an elastically contractible condition. The central portion of the elastic member between the first 118 and second end 120 may be attached to the garment facing surface of the liner either continuously or preferably intermittently along its length. In a particular embodiment, as best seen in FIGS. 1, 2, and 3–3b, the central portion is intermittently attached to the garment facing surface. As a result, the central portion of the elastic member will gather the unadhered liner portion and form a ruffled ridge.

Figure 5:
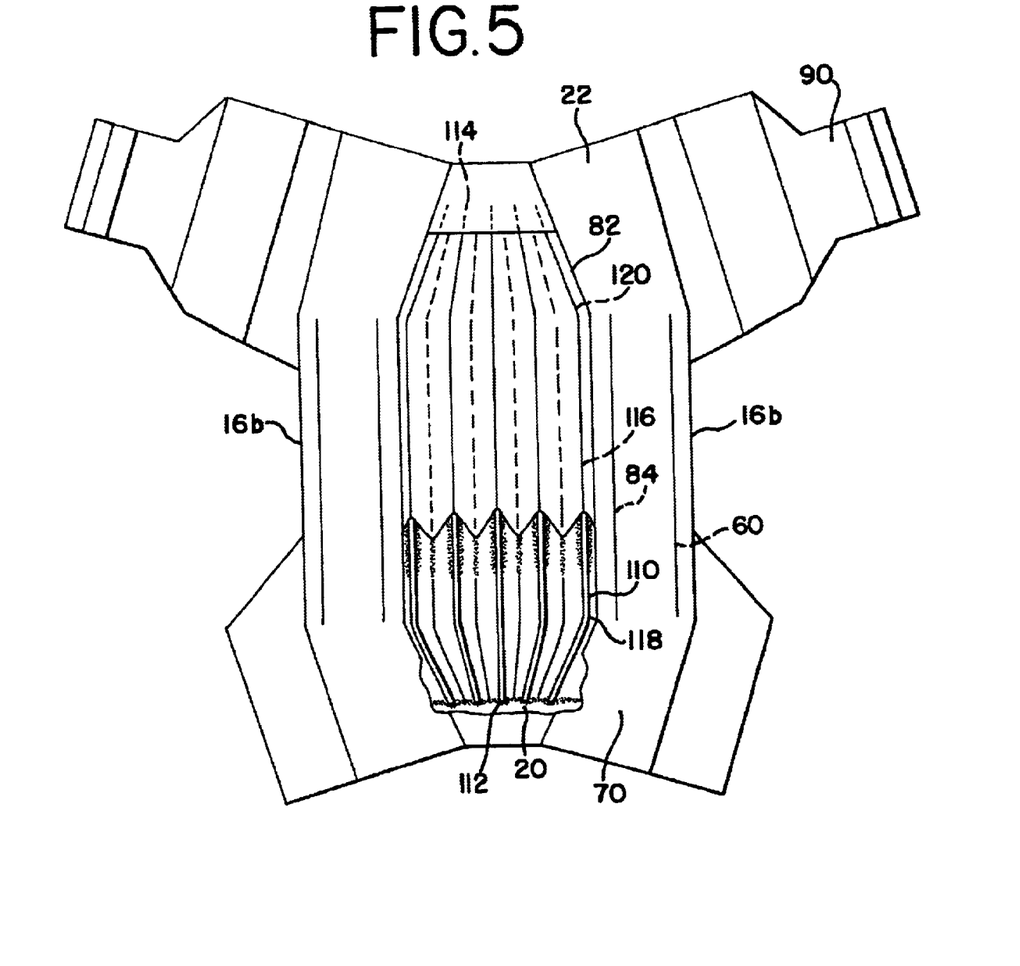
FIG. 5 is a top plan view of another embodiment of a disposable diaper of the present invention with a portion cut-away to reveal underlying structure. In this embodiment, the front and rear ends of the elastic members are affixed in the region of the front and rear waistband, respectively.

In one preferred embodiment, the front and rear ends are not attached, as best seen in FIG. 2. In another embodiment, shown in FIG. 5, the front end is anchored at the front waistband region and the rear end is anchored at the rear waistband region.

It should be understood that a wide range of changes and modifications can be made to the embodiments described above. It is therefore intended that the foregoing description illustrates rather than limits this invention and that it is the following claims, including all equivalents, which define this invention.

What is claimed is:

1. A disposable absorbent article with a front waistband and a back waistband being spaced from each other prior to installing the article on a wearer and a crotch portion disposed in a longitudinal direction between the front waistband and the back waistband and disposed in a lateral direction between a pair of leg openings, the article further comprising:
   a. a liquid impervious backsheet;
   b. a liquid pervious bodyside liner having a body faceable surface and an article faceable surface, wherein the article faceable surface has a plurality of spaced apart longitudinally extending adhered portions located in the crotch portion of the article to define a plurality of laterally alternating adhered and unadhered portions in the crotch portion of the article;
   c. an absorbent structure disposed between the liner and the backsheet; and,
   d. at least three elastic members disposed between the liner and the absorbent structure and comprising a front end, a rear end, and a central portion disposed between the front and rear ends with the central portion being in an elastically contractible condition, each of the elastic members associated with and positioned subjacent a respective one of the unadhered liner portions wherein each of the elastic members causes the respective associated superjacent unadhered liner portion to be spaced away from the absorbent structure forming at least three ridges and respective troughs defined between adjacent ones of the ridges.

2. The disposable absorbent article of claim 1 wherein the central portion of each of the elastic members includes a first end spaced from a second end with each of the first and second ends adhered to the liner.

3. The disposable absorbent article of claim 2 wherein the central portion of each of the elastic members between the first end and second end is intermittently adhered to the liner.

4. The disposable absorbent article of claim 1 wherein the front end and the rear end of each of the elastic members is in a relaxed state.

5. The disposable absorbent article of claim 1 wherein each ridge has substantially the same height.

6. The disposable absorbent article of claim 1 wherein the ridges have differing heights to define an inverted V-shaped profile of the crotch portion.

7. The disposable absorbent article of claim 1 wherein the adhered portions of the liner are directly adhered to the absorbent structure.

8. The disposable absorbent article of claim 1 wherein the central portion of each elastic member has substantially the same longitudinal length.

9. The disposable absorbent article of claim 1 wherein the at least some of the central portion of the elastic members have differing longitudinal lengths.

10. The disposable absorbent article of claim 1 wherein the article comprises a diaper and wherein the front and rear ends of the elastic members are in a relaxed condition such that the front and back waistbands assume a substantially flat position in the longitudinal direction so that the diaper lies substantially flat prior to installing the diaper on the wearer.

11. The disposable absorbent article of claim 1 wherein in the crotch portion at least some of the elastic members are uniformly spaced across the entire lateral width of the absorbent structure.

12. A disposable absorbent article comprising:
   a. an absorbent structure having an article faceable surface, a body faceable surface, and a pair of side edges;
   b. a backsheet associated with the absorbent structure on the article faceable surface, the backsheet defining a front waistband, a back waistband, a pair of leg openings, and a crotch portion disposed between and spaced from the front and back waistbands and disposed between the leg openings, wherein the front and back waistbands are spaced from each other prior to installing on a wearer;

c. a bodyside liner associated with the absorbent structure on the body faceable side of the absorbent structure, the liner having a body faceable surface and an article faceable surface with the article faceable surface having a plurality of spaced apart adhered portions located in the crotch portion of the article to define a plurality of alternating adhered and unadhered portions located in the crotch portion of the article;

d. a leg elastic member attached to the article near each of the leg openings thereby elasticizing each of the leg openings; and e. at least three elastic members disposed between the leg openings, the liner and absorbent structure subjacent a respective one of the unadhered portions of the liner and extending a portion of the distance from the front waistband to the back waistband, each elastic member having a first end spaced from a second end to define a central portion with the central portion being in an elastically contractible condition to cause the respective superjacent unadhered portion to be spaced away from the absorbent structure to form a respective ridge, the ridges extending longitudinally with a middle one of the ridges positioned approximately midway between the leg elastic members.

13. The disposable absorbent article of claim 12 wherein the article comprises a diaper and wherein front and rear ends of the elastic members are in a relaxed condition such that the front and back waistbands assume a substantially flat position in the longitudinal direction so that the diaper lies substantially flat prior to installing the diaper on the wearer.

14. The disposable absorbent article of claim 12 wherein in the crotch portion at least some of the elastic members are uniformly spaced across the entire lateral width of the absorbent structure.

15. A disposable absorbent article with a front waistband and a back waistband being spaced from each other prior to installing the article on a wearer, a crotch portion disposed in a longitudinal direction between the front waistband and the back waistband and disposed in a lateral direction between a pair of leg openings, the article further comprising:

a. a liquid impervious backsheet;

b. a liquid pervious bodyside liner having a body faceable surface and an article faceable surface, wherein the article faceable surface has a longitudinally extending corrugated surface located in the crotch portion formed from laterally alternating adhered and unadhered portions of the liner to define at least three ridges, wherein the corrugated surface provides a resistance against lateral migration of body exudates;

c. an absorbent structure disposed between the liner and the backsheet; and d. at least three elastic members disposed between the liner and the absorbent structure, each of the elastic members associated with and positioned and back waistbands assume a substantially flat position in the longitudinal direction prior to installing the article on the wearer.

16. The disposable absorbent article of claim 15 wherein the corrugated surface is formed by a plurality of ridges aligned substantially parallel to the longitudinal direction and wherein at least some of the ridges in the crotch portion are uniformly laterally spaced across the entire lateral width of the absorbent structure.

* * * * *